(12) United States Patent
Lipscombe et al.

(10) Patent No.: US 6,930,171 B2
(45) Date of Patent: Aug. 16, 2005

(54) RHAMNOSE BINDING PROTEIN

(75) Inventors: Richard J. Lipscombe, Perth (AU); Stephen John Carter, Woodvale (AU); Michael Ruane, Applecross (AU)

(73) Assignee: Solbec Pharmaceuticals Limited, Nedlands (AU)

( * ) Notice: Subject to any disclaimer, the term of this patent is extended or adjusted under 35 U.S.C. 154(b) by 22 days.

(21) Appl. No.: 10/359,873

(22) Filed: Feb. 7, 2003

(65) Prior Publication Data

US 2004/0030104 A1 Feb. 12, 2004

Related U.S. Application Data

(60) Provisional application No. 60/355,593, filed on Feb. 7, 2002.

(51) Int. Cl.$^7$ .............................. C07K 1/00; C07K 14/00
(52) U.S. Cl. ........................................ 530/350; 530/380
(58) Field of Search ................................... 530/350, 380

(56) References Cited

U.S. PATENT DOCUMENTS 5,225,542 A    7/1993 Cramer et al.

OTHER PUBLICATIONS

Tateno et al (Journal of Biological Chemistry vol. 273, No. 30, pp 19190–19197, Jul. 24, 1998).*

Grillon et al. "Soluble human lymphocyte sugar binding proteins with immunosuppressive activity". *Immunology Letters*, vol. 28, No. 1, pp. 47–56 (1991).

Weebadda et al. "Avian sac and plasma proteins that bind surface polysaccharides of *Escherichia coli* O2". *Comparative Biochemistry and Physiology*, Part B, vol. 130, pp. 299–312 (2001).

Komori et al. "Primary structure and biological active of snake venom lectin (APL) from *Agkistrodon p. piscivorus* (eastern cottonmouth)", *Toxicon*, vol. 37, pp. 1053–1064 (1999).

Amini et al. "Cryptic domains of a 60kDa heat shock protein of *Helicobacter pylori* bound to bovine lactoferrin". *FEMS Immunology and Medical Microbiology*, vol. 16, pp. 247–255 (1996).

Nitta et al. "Comparative studies of carbohydrate–binding proteins from *Xenopus laevis* skin and eggs. Sugar–binding specificities and affinity purification". *Chemical and Pharmaceutical Bulletin*, vol. 38, No. 4, pp. 975–981 (1990).

Tobin et al. "Purification and properties of RhaR, the positive regulator of the L–Rhamnose operons of *Escherichia coli*". *Journal of Molecular Biology*, vol. 211, pp. 75–89 (1990).

Daikohara et al. "Comparative studies of the agglutination of tumor cells and erythrocytes by *Plecoglossus altivelis* (Ayu fish) roe lectin". *Physio–chemical Biology*, vol. 37, No. 1, pp. 31–40 (1993).

Kolb–Bachofen et al. "GalNAc/Gal–specific rat liver lectins: their role in cellular recognition". *Biology Cell*, vol. 51, pp. 219–226 (1984).

Lehrman et al. "The binding of fucose–containing glycoproteins by hepatic lectins". *The Journal of Biological Chemistry*, vol. 261, pp. 7412–7418 (Jun. 1986).

Ashwell et al. "Carbohydrate–specific receptors of the liver". *Ann. Rev. Biochem*, vol. 51, pp. 531–554 (1982).

* cited by examiner

*Primary Examiner*—Mark Navarro
(74) *Attorney, Agent, or Firm*—Merchant & Gould P.C.

(57) ABSTRACT

An isolated RBP with at least one of the following characteristics:
  a) a molecular weight of approximately 65–70 kDa and more preferably 66–69 kDa;
  b) a pI of greater than 10 or less than 3;
  c) a dissociation constant of approximately $1.5\times10^{-6}$ when bound to the rhamnose moiety of solamargine;
  d) adapted to bind to a rhamnose affinity column prepared according to example 1 and under the conditions set out therein;
  e) adapted to be eluted from the column in example 1 with a 100 mM rhamnose solution;
  f) insoluble in aqueous solution; and
  g) soluble in highly denaturing buffers containing greater that approximately 2% surfactant.

9 Claims, 13 Drawing Sheets

Figure 2
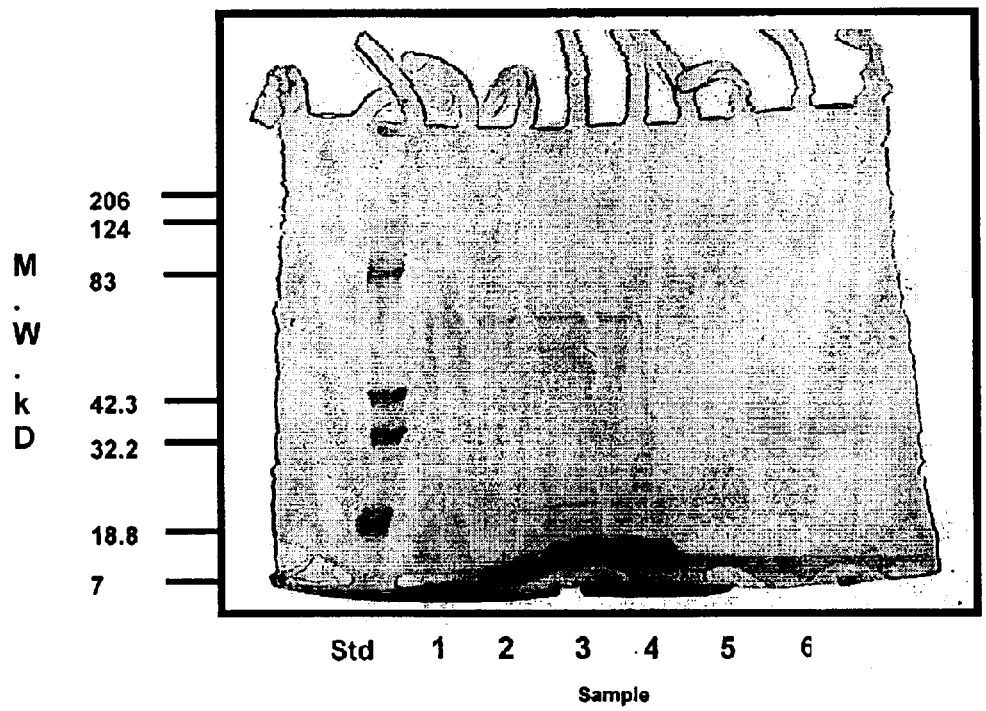
A
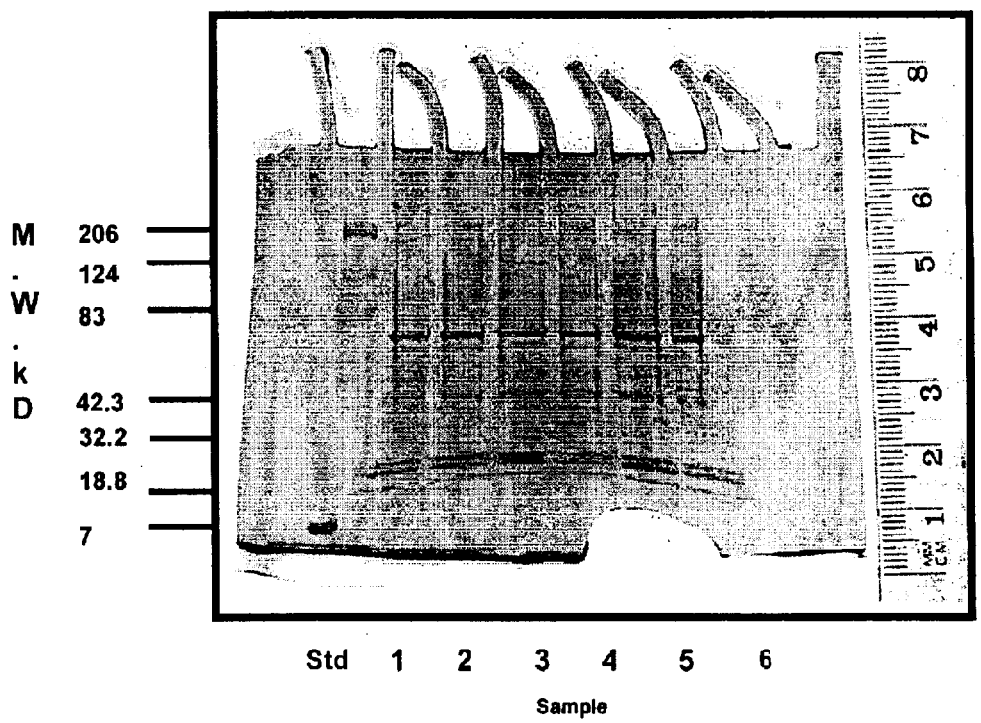
B

Figure 8

[Chart: BEC dose/cell at LD50 vs x-axis (0 to 10000)]

- Susceptible
- Less susceptible

REGION 1
Predominant parameter is receptor affinity

REGION 2
Predominant parameter is number of receptors per cell

Figure 9

| Cell line | Type | Cell number | LD50 BEC, ug/mL | Background |
|---|---|---|---|---|
| AGS | Gastric carcinoma | 1250 | 6.85 +/- 0.10 | 4.34 +/- 0.89 |
| MIA PaCa-2 | Carcinoma, pancreas | 2500 | 11.40 +/- 0.14 | 7.54 +/- 1.64 |
| 786-O | Renal cell adenocarcinoma | 625 | 4.95 +/-0.04 | 2.99 +/- 0.32 |
| HeLa 229 | Adenocarcinoma, uterine cervix | 5000 | 7.63 +/- 0.09 | 0.65 +/- 0.83 |
| HepG2 | Hepatocellular carcinoma | 10000 | 6.37 +/- 0.19 | 2.45 +/- 1.65 |
| JAM | Ovarian carcinoma | 3750 | 7.32 +/- 0.16 | 0.35 +/- 1.65 |
| NO36 | Mesothelioma | 2500 | 6.98 +/- 0.11 | 2.41 +/- 1.20 |
| U87-MG | Glioblastoma, astrocytoma | 10000 | 10.99 +/- 0.38 | 8.29 +/- 4.01 |
| DV145 | Prostate carcinoma | 2500 | 6.78 +/- 0.15 | 1.83 +/- 1.72 |
| LNCaP | Prostate adenocarcinoma (met) | 7500 | 7.97 +/- 0.18 | 5.50 +/- 1.91 |
| A2058 | Melanoma (met) | 5000 | 7.05 +/- 0.09 | 0.81 +/- 0.92 |

A2058, 600 cells

A2058, 5000 cells

RHAMNOSE BINDING PROTEIN

This application claims the benefit of U.S. Provisional Application No. 60/355,593 field Feb. 7, 2002.

FIELD OF THE INVENTION

The present invention relates to an isolated rhamnose binding protein (RBP) that is over expressed in cancer cells relative to non-cancer cells. The present invention also relates to methods of diagnosing cancer by detecting RBP levels and to RBP agonists such as antibodies and methods of treating and diagnosing cancer using RBP agonists.

BACKGROUND ART

BEC® is a mixture of the triglycosides: solasonine and solamargine that has anti-cancer activity. Studies on the mode of action of BEC® indicate that the glycosides gain entry to cancer cells via a cell surface receptor and that the in vitro toxicity of BEC® to cancer cells is reduced by co-administration of rhamnose.

The presence of endogenous endocytic ligand receptors (EEL) has been an area of clinical research for over 2 decades. The first EEL to be identified was the asialoglycoprotein receptor on mammalian hepatocytes with specificity for galactose (Ashwell & Hardford 1982). Since this time other hepatic receptors have been identified. For example, fucose (Lehrman et al 1986), GalNAc (Kolb-Bachofen etal 1984), as well as a number of cell receptors identified by Cramer and Gabius (1991). EEL's may be involved in cellular recognition, cell adhesion or substrate binding.

To date no one has isolated and/or characterised the cell surface receptor that is central to BEC®'s mode of action. The present invention seeks to overcome or at least partially alleviate this problem.

SUMMARY OF THE INVENTION

The present invention provides an isolated RBP with at least one of the following characteristics:

(a) a molecular weight of approximately 65–70 kDa and more preferably 66–69 kDa;

(b) a pI of greater than 10 or less than 3;

(c) a dissociation constant of approximately $1.5 \times 10^{-6}$ when bound to the rhamnose moiety of solamargine;

(d) adapted to bind to a rhamnose affinity column prepared according to example 1 and under the conditions set out therein;

(e) adapted to be eluted from the column in example 1 with a 100 mM rhamnose solution;

(f) insoluble in aqueous solution; and (g) soluble in highly denaturing buffers containing greater that approximately 2% surfactant.

The ability of the RBP to bind ligands such as rhamnose to a RBP bearing cell, such as a carcinoma, render it useful in various methods. For example, it has been found that when the RBP binds a ligand, such as rhamnose, cell adhesion of the RBP bearing cells is inhibited. Thus, the present invention also provides a method of inhibiting cell adhesion between RBP bearing cells comprising the step of contacting the RBP bearing cells with an effective amount of a RBP ligand. The effective amount may be varied depending on the circumstances and may be determined by those skilled in the art. However, when the RBP ligand is rhamnose the effective amount may be approximately 70 picograms/cell.

Upon binding of a ligand to a cell associated RBP of the present invention, depending on the ligand, the ligand may be internalised in the cell or remain on the cell surface. Whether or not a ligand is internalised after binding to a cell associated RBP of the present invention depends on a variety of factors such as the molecular weight, charge, structure and/or biological activity of the ligand.

Thus, the present invention also provides a method of delivering an agent to a RBP bearing cell comprising contacting an agent-ligand complex with the RBP bearing cell.

The agent may be delivered to the cell surface or inside the cell by selecting an appropriate ligand-agent complex. For example, by selecting an agent-complex of a certain molecular weight or structure it is possible to control the delivery of the agent to the cell surface or the inside of the cell. In this regard, it has been found that if the agent is above a certain threshold weight then it cannot be efficiently internalised in by the RBP bearing cell and will remain at the cell surface.

The ability of RBP to bind ligands and either internalise or retain them on a cell surface, means the RBP may be utilised to locate and identify RBP bearing cells. Thus, the present invention also provides a method of detecting a RBP bearing cell comprising the steps of: (i) contacting a cell or tissue sample with an agent adapted to selectively bind to RBP and (ii) detecting the RBP bearing cells.

The agent may be varied and includes antibodies and other ligands or agonists that are adapted to bind to RBP. Furthermore, to ease detection of the RBP bearing cells the agent may be adapted to be visualised.

Thus, the RBP of the present invention may be used to identify agents that bind to the RBP and thus can be used in assays for the RBP, as diagnostics to identify RBP bearing cells or to target therapeutic agents to cancer cells via the RBP. The RBP may also form a component of a screening system for antagonists or agonists of agents that bind to the RBP.

These and additional uses for the reagents described herein will become apparent to those of ordinary skill in the art upon reading this specification.

BRIEF DESCRIPTION OF THE FIGURES

FIG. 2A: is a fluoro-image of proteins crosslinked to FRITC and analysed on a 4–20% polyacrylamide gel. Standards (tagged with assorted coloured dyes hence some visible by fluoro-imaging); Sample: 1) 5 μM FRITC (Batch 1)+100 μM CDI; 2) 5 μM FRITC+500 μM CDI; 3) 5 μM FRITC+10 mM CDI; 4) 5 μM FRITC (Batch 2)+100 μM CDI; 5) No FRITC+100 μM CDI; 6) No FRITC+500 μM CDI;

FIG. 2B: is the total proteins from the gel depicted in FIG. 2A stained with Coomassie brilliant blue;

FIG. 8: is a comparison of the plots in FIGS. 6 and 7;

FIG. 9: is table containing single point LD50 data from another 11 carcinomas;

Figure 1:
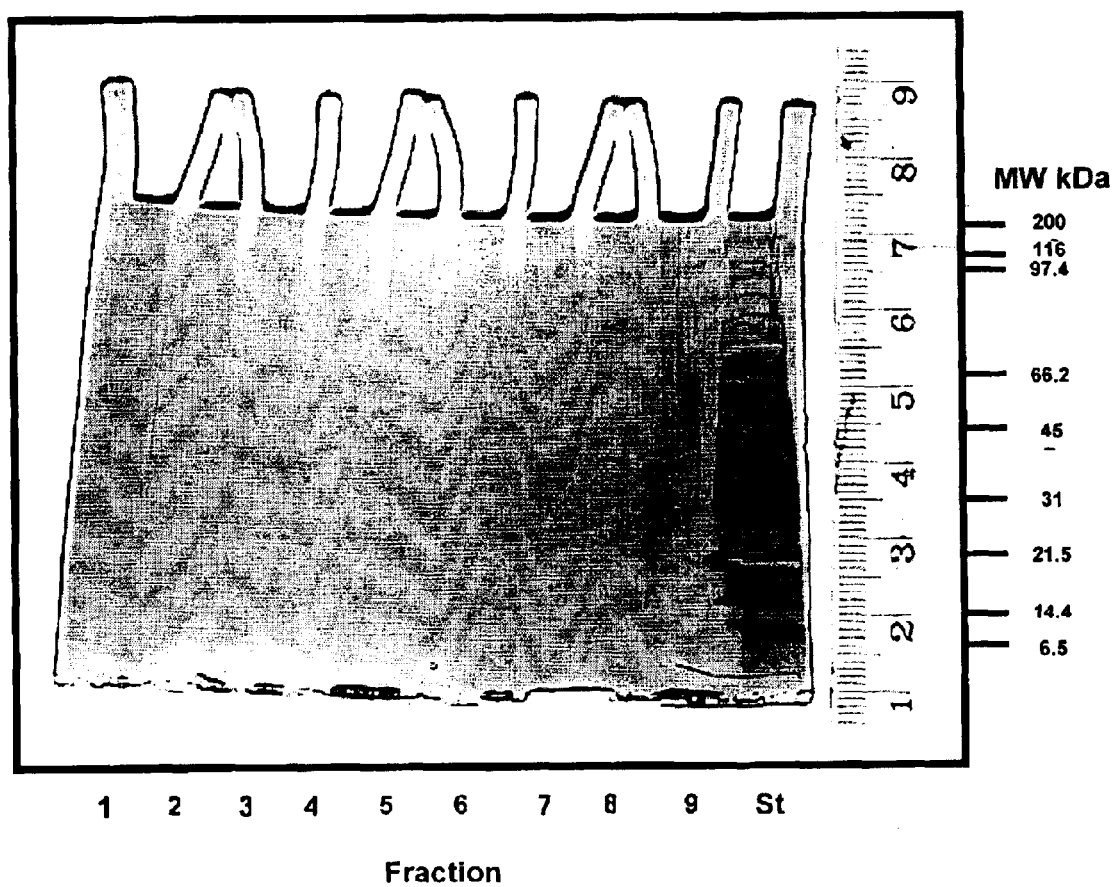
FIG. 1: depicts a PAGE gel containing fractions 1–9 eluted from a biotinylated rhamnose-ITC affinity column using 100 mM free rhamnose and lane 10 contains standard molecular weight markers.

Total protein stain—Lane 1: Standards 206, 124, 83, 42.3, 32.2, 18.8 kD; Both); Lane 2 Protein A pre-clear (-ve); Lane 3 $\alpha$-FITC antibody precipitation

DETAILED DESCRIPTION OF THE INVENTION

Rhamnose Binding Protein (RBP)

The present invention is based on the isolation and identification of a cellular receptor of the lectin group that is more abundant on neoplastic (cancer) cells than non-cancer cells. The receptor ("RBP") is adapted to bind and internalise rhamnose and thus represents a valuable diagnostic and therapeutic tool.

The present invention provides an isolated RBP comprising at least one of the following characteristics:

(a) a molecular weight of approximately 65–70 kDa and more preferably 66–69 kDa;

(b) a pI of greater than 10 or less than 3;

(c) a dissociation constant of approximately $1.5 \times 10^{-6}$ when bound to the rhamnose moiety of solamargine;

(d) adapted to bind to a rhamnose affinity column prepared according to example 1 and under the conditions set out therein;

(e) adapted to be eluted from the column in example 1 with a 100 mM rhamnose solution;

(f) insoluble in aqueous solution; and (g) soluble in highly denaturing buffers containing greater that approximately 2% surfactant.

Throughout the specification, unless the context requires otherwise, the word "comprise" or variations such as "comprises" or "comprising", will be understood to imply the inclusion of a stated integer or group of integers but not the exclusion of any other integer or group of integers.

The RBP and other polypeptides of the invention may be in a substantially isolated form. In this regard, it will be understood that they may be mixed with carriers or diluents that will not interfere with their intended purpose and still be regarded as substantially isolated. A polypeptide of the invention may also be in a substantially purified form, in which case it will generally comprise the polypeptide in a preparation in which at least 90%, 95%, 98% or 99% of the protein in the preparation is a polypeptide of the invention.

Assays for Compounds That Bind RBP

The RBP of the present invention may be used in assays to identify compounds that interact with (e.g., bind to) it.

The compounds which may be screened in accordance with the invention include, but are not limited to peptides, antibodies and fragments thereof, and other organic compounds (e.g., peptidomimetics) that bind to the RBP and either mimic the activity triggered by the natural ligand—rhamnose (i.e., agonists) or inhibit the activity triggered by the natural ligand—rhamnose (i.e., antagonists).

Other compounds that may be screened according to the present invention are peptides, antibodies or fragments thereof, and other organic compounds that mimic the extra cellular domain of the RBP (or a portion thereof) and bind to and "neutralize" natural ligand such as rhamnose.

Such compounds may include, but are not limited to, peptides such as, for example, soluble peptides, including but not limited to members of random peptide libraries; and combinatorial chemistry-derived molecular library made of D- and/or L-configuration amino acids, phosphopeptides including, but not limited to, members of random or partially degenerate, directed phosphopeptide libraries, antibodies (including, but not limited to, polyclonal, monoclonal, humanized, anti-idiotypic, chimeric or single chain antibodies, and FAb, F(ab').sub.2 and FAb expression library fragments, and epitope-binding fragments thereof), and small organic or inorganic molecules.

Computer modelling and searching technologies permit identification of compounds, or the improvement of already identified compounds, that can modulate RBP expression or activity. Having identified such a compound or composition, the active sites or regions are identified. Such active sites might typically be ligand binding sites, such as the interaction domains of rhamnose with RBP itself. The active site can be identified using methods known in the art including, for example, from study of complexes of RBP with rhamnose. In this regard, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances.

Having determined the structure of the active site, either experimentally, by modelling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential RBP modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modelling methods useful to identify modulating compounds based upon identification of the active sites of rhamnose and RBP will be apparent to those of skill in the art.

Although described above with reference to design and generation of compounds that could alter binding, one could also screen libraries of known compounds, including natural products or synthetic chemicals, and biologically active materials, including proteins, for compounds that are inhibitors or activators.

Compounds identified via assays such as those described herein may be useful, for example, in elaborating the biological function of the RBP and for treating cancer.

The compounds capable of binding RBP may also be used to identify and isolate RBP homologues. In this regard, the compounds may be used to screen various cell types such as cancer cell types to locate variants of the RBP that could be used to design specific therapeutic agents for treatment of related cancers.

In vitro systems may be designed to identify compounds capable of interacting with (e.g., binding to) RBP (including, but not limited to, the extra cellular domain of RBP). These compounds may be useful, for example, in modulating the activity of wild type and/or mutant RBP; elaborating the biological function of the RBP; screening for compounds that disrupt normal RBP interactions; or may in themselves disrupt such interactions.

The principle of the assays used to identify compounds that bind to the RBP involves preparing a reaction mixture of the RBP and the test compound under conditions and for a time sufficient to allow the two components to interact and bind, thus forming a complex which can be removed and/or detected in the reaction mixture. The RBP species used can vary depending upon the goal of the screening assay. For example, where agonists of the natural ligand are sought, the full length RBP, or a soluble truncated RBP, e.g., in which the transmembrane or cellular domain is deleted from the molecule, a peptide corresponding to the extracellular domain or a fusion protein comprising the RBP extracellular domain fused to a protein or polypeptide that affords advantages in the assay system (e.g., labelling, isolation of the resulting complex, etc.) can be utilized.

The screening assays can be conducted in a variety of ways. For example, one method to conduct such an assay involves anchoring the RBP or fusion protein or the test substance onto a solid phase and detecting RBP/test compound complexes anchored on the solid phase at the end of the reaction. In one embodiment of such a method, the RBP may be anchored onto a solid surface, and the test compound, which is not anchored, may be labelled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the RBP or test compound and drying. Alternatively, an immobilized antibody, such as a monoclonal antibody, specific for the protein to be immobilized may be used to anchor the protein to the solid surface.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labelled, the detection of label immobilized on the surface indicates that complexes were formed. Where the previously nonimmobilized component is not pre-labelled, an indirect label can be used to detect complexes anchored on the surface; e.g., using a labelled antibody specific for the previously nonimmobilized component (the antibody, in turn, may be directly labelled or indirectly labelled with a labelled anti-Ig antibody).

Alternatively, a reaction can be conducted in a liquid phase, the reaction products separated from unreacted components, and complexes detected; e.g., using an immobilized antibody specific for RBP or the test compound to anchor any complexes formed in solution, and a labelled antibody specific for the other component of the possible complex to detect anchored complexes.

Cell-based assays can also be used to identify compounds that interact with RBP. To this end, cell lines that naturally express RBP such as a cancer cell line selected from the group comprising: HT-29, LS174-T. AGS, 5637, A431, 786-O, Hs578Bst, CCD 18Lu, HeLa 229, HepG2, JAM, $NO_{36}$, U87-MG, DV145, LNCaP and A2058, or cell lines (e.g., COS cells, CHO cells, fibroblasts, etc.) that have been genetically engineered to express RBP (e.g., by transfection or transduction of RBP DNA) can be used. Interaction of the test compound with, for example, the extracellular domain of RBP expressed by the host cell can be determined by comparison or competition with native rhamnose.

Diagnostics

The RBP of the present invention and agonists thereof can be employed for the diagnostic and prognostic evaluation of cancer. Such methods may, for example, utilize reagents such as the antibodies described herein. Specifically, such reagents may be used, for example, to detect an over-abundance of RBP relative to normal cells.

Thus, the present invention provides a method for detecting cancer in a sample comprising the steps of: (i) detecting the level of RBP in the sample; and (ii) comparing it to the level of RBP in a sample from a non-cancer source.

The detection method of the present invention may be used to diagnose cancer in vitro. Thus, the present invention provides a method of diagnosing cancer in a patient comprising the steps of: (i) detecting the level of RBP in a sample from the patient; and (ii) comparing it to the level of RBP in a sample from a non-cancer source.

Alternatively, the detection method may be used to diagnose cancer in vivo. In this regard, agents that are adapted to bind to RBP can be labelled and administered to a subject suspected of having cancer and later detected to perform the diagnosis. Thus, the present invention also provides a method of diagnosing cancer in a patient comprising the steps of: (i) detecting the level and/or distribution of RBP in the patient; and (ii) analysing the distribution and/or levels of RBP to identify differences that are indicative of cancer.

The methods described herein may be performed, for example, by utilizing prepackaged diagnostic kits comprising at least one specific RBP antibody reagent described herein, which may be conveniently used, e.g., in clinical settings, to diagnose patients suspected of having cancer.

RBP antibodies and other agonists of RBP may be used as cancer diagnostics and prognostics, as described herein. Such diagnostic methods may be used to detect abnormalities in the level of RBP and may be performed in vivo or in vitro, such as, for example, on biopsy tissue.

For example, antibodies directed to epitopes of the RBP can be used in vivo to detect the pattern and level of expression of the RBP in the body. Such antibodies can be labelled, e.g., with a radio-opaque or other appropriate compound and injected into a subject in order to visualize binding to the RBP expressed in the body using methods such as X-rays, CAT-scans, or MRI. Labelled antibody fragments, e.g., the Fab or single chain antibody comprising the smallest portion of the antigen binding region may also be used for this purpose. When interpreting the patterns produced according to the diagnostic method, account must be taken on background signal or "noise" from non-cancer cells that also bear the RBP, albeit at lower levels. However, those skilled in the art are readily able to discern noise from actual signal in performing the diagnosis. Immunoassays or fusion protein detection assays can also be used to diagnose or type cancer in biopsy or autopsy samples in vitro.

Agonists described herein including antibodies, or fragments of antibodies may also be used to quantitatively or qualitatively detect the presence of RBP or conserved variants or peptide fragments thereof. This can be accomplished, for example, by immunofluorescence techniques employing a fluorescently labelled antibody coupled with light microscopic, flow cytometric, or fluorimetric detection.

The agonists such as antibodies (or fragments thereof) of the present invention may, additionally, be employed histologically, as in immunofluorescence, immunoelectron microscopy or non-immuno assays, for in situ detection of RBP or conserved variants or peptide fragments thereof.

In situ detection may be accomplished by removing a histological specimen from a patient, and applying thereto a labelled antibody or fusion protein of the present invention. The antibody (or fragment) or fusion protein is preferably applied by overlaying the labelled antibody (or fragment) onto a biological sample. Through the use of such a procedure, it is possible to determine not only the presence of the RBP, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for RBP or conserved variants or peptide fragments thereof will typically comprise incubating a sample, such as a biological fluid, a tissue extract, freshly harvested cells, or lysates of cells which have been incubated in cell culture, in the presence of a detectably labelled antibody capable of identifying RBP or conserved variants or peptide fragments thereof, and detecting the bound antibody by any of a number of techniques well-known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labelled RBP antibody or other agonist. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

With respect to antibodies, one of the ways in which the antibody can be detectably labelled is by linking the same to an enzyme. This then renders the antibody suitable for use in an enzyme immunoassay (EIA). The enzyme that is bound to the antibody will react with an appropriate substrate, preferably a chromogenic substrate, in such a manner as to produce a chemical moiety that can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alphaglycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labelling the antibodies, antibody fragments or other agonists, it is possible to detect RBP through the use of a radioimmunoassay (RIA). The radioactive isotope can be detected by such means as the use of a gamma counter or a scintillation counter or by autoradiography.

It is also possible to label the antibody or other agonist with a fluorescent compound. When the fluorescently labelled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

Agonists such as antibodies can also be detectably labelled using fluorescence emitting metals such as $^{152}$Eu, or others of the lanthanide series. These metals can be attached to the antibody using such metal chelating groups such as diethylenetriaminepentacetic acid (DTPA) or ethylenediaminetetraacetic acid (EDTA).

The antibody or other agonist can also be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labelling compounds are luminol, isoluminol, theromatic acridinium ester, imidazole, acridinium salt and oxalate ester.

Likewise, a bioluminescent compound may be used to label the antibody or other agonist of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labelling are luciferin, luciferase and aequorin.

Methods of Treatment

The ability of the agonists of the present invention bind to RBP and subsequently become internalised in the target cell renders them useful for preferentially delivering agents to cells with a higher load of RBP, such as cancer cells.

For therapeutic purposes, the agents linked to the agonists of the present invention may be any agent that is adapted to prevent cell growth or division or cause cell death such as, Doxorubicin, Daunorubicin, Vincristine, Vimblastine, Vindesine, Methothrexate, Cytarabine, Etopside, Cisplatin, Carboplatin, 5-Fluorouracil, Bleomycin, Epirubicin, Cyproterone, Irinotecan etc. When linked to such agents the agonists of the present invention may be used to treat cancer in a patient.

Thus, the present invention provides a method of treating cancer in a subject comprising administering a therapeutically effective amount of a RBP agonist anticancer conjugate to said subject.

The agonists of the present invention may also be used to treat BEC® overdose. In this regard, if BEC® has been administered to a patient at too high a dose, then an agonist of the present invention may be administered to bind to the RBP of the present invention and prevent or at least reduce BEC® binding.

Thus, the present invention also comprises a method of treating BEC® overdose in a subject, the method comprising administering an effective amount of an RBP agonist to the subject. Agonists for use in this aspect of the invention may be varied and include RBP antibodies, rhamnose or some other RBP ligand.

Compositions/Administration

This invention also contemplates pharmaceutical or veterinary compositions comprising an agonist of the present invention and a pharmaceutically acceptable carrier. Preferably, the compositions will further comprise an agent adapted to cause cell death such as a glycoside. Pharmaceutical compositions of proteineous drugs of this invention are particularly useful for parenteral administration, i.e., subcutaneously, intramuscularly or intravenously. The compositions for parenteral administration may comprise a solution of the compounds of the invention or a cocktail thereof dissolved in an acceptable carrier, preferably an aqueous carrier, an emulsion or formulated as micelles in an appropriate carrier. A variety of aqueous carriers may be employed, e.g., water, buffered water, 0.4% saline, 0.3% glycine, and the like. These solutions are preferably sterile and generally free of particulate matter. These solutions may be sterilized by conventional, well known sterilization techniques. The compositions may further contain pharmaceutically acceptable auxiliary substances as required to approximate physiological conditions such as pH adjusting and buffering agents.

The concentration of the compounds of the invention in such pharmaceutical formulation can very widely, i.e., from less than about 0.1%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

In situations where the agonist is non-proteineous, it may be administered alone or in combination with pharmaceutically acceptable carriers. The proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered sublingually in the form of troches or lozenges in which the active ingredient is mixed with fillers and binders, flavouring agents and dyes; and then dehydrated sufficiently to make it suitable for pressing into a solid form. They may be administered orally in the form of solutions that may be injected parenterally, that is, intramuscularly, intravenously or subcutaneously. For parenteral administration, they may be used in the form of a sterile solution containing other solutes, for example, enough saline or glucose to make the solution isotonic.

The physician or veterinarian will determine the dosage of the present therapeutic agents that will be most suitable and it will vary with the form of administration and the particular compound chosen, and furthermore, it will vary with the particular subject under treatment. The physician will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other serotonergic agents and the dosage level is of the same order of magnitude as is generally employed with these other therapeutic agents. The therapeutic dosage will generally be from 1 to 1000 milligrams per day and higher although it may be administered in several different dosage units. Tablets containing from 5 to 100 mg. of active agent are particularly useful.

Topical Administration

The pharmaceutical compositions of the present invention may be adapted for topical application to a patient.

Various topical delivery systems may be appropriate for administering the compositions of the present invention depending upon the preferred treatment regimen. Topical formulations may be produced by dissolving or combining the agonist of the present invention in an aqueous or nonaqueous carrier. In general, any liquid, cream, or gel, or similar substance that does not appreciably react with the agonist or any other of the active ingredients that may be introduced into the composition and which are non-irritating are suitable. Appropriate non-sprayable viscous, semi-solid or solid forms can also be employed that include a carrier compatible with topical application and have a dynamic viscosity preferably greater than water.

Suitable formulations are well known to those skilled in the art and include, but are not limited to, solutions, suspensions, emulsions, creams, gels, ointments, powders, liniments, salves, aerosols, transdermal patches, etc, which are, if desired, sterilized or mixed with auxiliary agents, e.g., preservatives, stabilizers, emulsifiers, wetting agents, fragrances, colouring agents, odour controllers, thickeners such as natural gums etc. Particularly preferred topical formulations include ointments, creams or gels.

Ointments generally are prepared using either (1) an oleaginous base, i.e., one consisting of fixed oils or hydrocarbons, such as white petroleum or mineral oil, or (2) an absorbent base, i.e., one consisting of an anhydrous substance or substances which can absorb water, for example anhydrous lanolin. Customarily, following formation of the base, whether oleaginous or absorbent, the active ingredient is added to an amount affording the desired concentration.

Creams are oil/water emulsions. They consist of an oil phase (internal phase), comprising typically fixed oils, hydrocarbons and the like, waxes, petroleum, mineral oil and the like and an aqueous phase (continuous phase), comprising water and any water-soluble substances, such as added salts. The two phases are stabilised by use of an emulsifying agent, for example, a surface active agent, such as sodium lauryl sulfite; hydrophilic colloids, such as acacia colloidal clays, veegum and the like. Upon formation of the emulsion, the agonist is customarily added in an amount to achieve the desired concentration.

Gels comprise a base selected from an oleaginous base, water, or an emulsion-suspension base. To the base is added a gelling agent that forms a matrix in the base, increasing its viscosity. Examples of gelling agents are hydroxypropyl cellulose, acrylic acid polymers and the like. Customarily, the agonist is added to the formulation at the desired concentration at a point preceding addition of the gelling agent.

The amount of compound incorporated into a topical formulation is not critical; the concentration should be within a range sufficient to permit ready application of the formulation to the affected tissue area in an amount that will deliver the desired amount of agonist to the desired treatment site.

The customary amount of a topical formulation to be applied to an affected tissue will depend upon an affected tissue size and concentration of the agonist in the formulation.

In therapeutic applications, compositions of the invention are administered to a subject afflicted with cancer in an amount sufficient to at least improve the condition of the patient and preferably cure the patient of cancer.

Single or multiple administrations of the compositions can be carried out with dose levels and pattern being selected by the treating physician or veterinarian. In any event, the composition of the invention should provide a quantity of the compounds of the invention sufficient to effectively treat the cancer in the subject.

Antibodies

Antibodies that specifically recognize one or more epitopes of RBP, or epitopes of conserved variants of RBP, or peptide fragments of the RBP are also encompassed by the invention. Such antibodies include but are not limited to polyclonal antibodies, monoclonal antibodies (mAbs), humanized or chimeric antibodies, single chain antibodies, Fab fragments, F(ab').sub.2 fragments, fragments produced by a Fab expression library, anti-idiotypic (anti-Id) antibodies, and epitope-binding fragments of any of the above.

The antibodies of the invention may be used, for example, in the detection of the RBP in a biological sample and may, therefore, be utilized as part of a diagnostic or prognostic technique whereby patients may be tested for abnormal amounts of RBP. Such antibodies may also be utilized in conjunction with, for example, compound screening schemes, as described herein for evaluating the effect of test compounds on the ability of RBP to bind its ligand. Additionally, such antibodies may be used to inhibit RBP activity that may be useful in various studies on the dynamics of the binding between the RBP and its ligand.

For the production of antibodies, host animals may be immunized by injection with the RBP or an immunogenic portion thereof such as one corresponding to a functional domain of the RBP, e.g. the extracellular domain. Host animals may include but are not limited to rabbits, mice, and rats, to name but a few.

Various adjuvants may be used to increase the immunological response, depending on the host species, including but not limited to Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies may be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the monoclonals of this invention may be cultivated in vitro or in vivo. Production of high titres of monoclonals in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against the RBP. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab').sub.2 fragments which can be produced by pepsin digestion of the antibody molecule and the Fab fragments which can be generated by reducing the disulfide bridges of the F(ab').sub.2 fragments. Alternatively, Fab expression libraries may be constructed (Huse et al., 1989, Science, 246:1275–1281) to allow rapid and easy identification of monoclonal Fab fragments with the desired specificity.

Antibodies to the RBP can, in turn, be utilized to generate anti-idiotype antibodies that "mimic" the RBP, using techniques well known to those skilled in the art. (See, e.g., Greenspan & Bona, 1993, FASEB J 7(5): 437–444; and Nissinoff, 1991, J. Immunol. 147(8):2429–2438). For example, antibodies that bind to the RBP and competitively inhibit the binding of rhamnose to the RBP can be used to generate anti-idiotypes that "mimic" the extracellular domain of the RBP and therefore bind rhamnose.

The present invention will now be described with reference to a number of examples. The examples are in no way limiting on the preceding description.

EXAMPLES

Example 1

Isolation of a Rhamnose Binding Protein Using Affinity Chromatography

Materials/Methods

1. Labelling of Rhamnose Probes

Biotin Rhamnose-ITC (BRITC) was formed by dissolving Rhamnose-ITC (Sigma R6881; RMM 297.3) in DMSO, diluting it to 1 mg/ml in 10 mM sodium bicarbonate pH 9.1 and then adding biotin hydrazide (Sigma, RMM 258.3) at 1:1 or 5:1 molar ratio and allowing the reaction to proceed at room temperature for 16 h.

2. Preparation of Rhamnose Affinity Column

Streptavidin sepharose conjugated columns (Amersham 17-5112-01) or free resin (17-5113-01) with a theoretical capacity for biotin labelled rhamnose (BRITC) of 60 $\mu$g/ml was used. An excess amount of BRITC was dissolved in phosphate buffered saline (PBS) and circulated over the pre-equilibrated column at a flow rate of 0.2 ml/min for 30 min. Successful coupling of the BRITC was monitored by HPLC analysis of the BRITC-PBS solution.

3. Cell Lysis

Packed, washed cells were lysed by freeze thawing (−80° C./4° C.) followed by brief sonication (30–40 sec at 50% duty pulse using 375W sonicator fitted with microtip probe). Cells were lysed in the presence of protease inhibitor cocktail (Roche 1-836-170) in order to minimise proteolysis.

4. Multiple Surfactant Solution (MSS)

MSS comprises 5 M urea, 2 M thiourea, 0.002 M n-tributyl phosphine, 0.5% pH 3–10 Pharmalyte carrier ampholytes (Pharmacia, Uppsala) [only in 2-D preparations], 2% 3-([3-cholamidopropyl]- dimethylammonio)-1-propanesulfonate (CHAPS), 2% caprylyl sulfo-betaine, and 0.001% Orange G dye. Material was also treated with endonuclease EC 3.1.30.2 in order to eliminate contaminating DNA.

5. One-dimensional Polyacrylamide Gel Electrophoresis (1D-PAGE)

Pre-cast Tris-HCl 4–20% polyacrylamide gradient gels (Bio-Rad) were used with electrode buffer Tris/glycine, pH 8.3. Sample loading solution: Tris pH 6.8, 0.1% SDS, glycerol, dithiothreitol, bromophenol blue marker.

Electrophoresis conditions: 100V for 90 min.

6. Protein Visualisation In-Gel

This was accomplished either by staining with silver, or with Coomassie R250 in water/methanol/acetic acid. Fluorescence was visualised using a Fluoro-imager (Pharmacia).

7. Affinity Chromatography

Whole cell lysis preparations were prepared using MSS on $10^8$–$10^9$ A2058 cells. The solubilised protein was then diluted 1/50 into HEPES buffered saline containing 140 mM NaCl, 2 mM $MgCl_2$, and 2 mM $CaCl_2$, pH 7.4 ($HBS^{2+}$) and passed sequentially over a control column (no rhamnose) and the rhamnose affinity column. Each column was washed with $HBS^{2+}$ and eluted with 100 mM rhamnose. Fractions were analysed using acrylamide mini-gels and 1D SDS-PAGE, followed by silver staining.

Results

A band with a molecular weight of approximately 65 kD was visualised in the eluent fractions (FIG. 1). No bands were visible in eluent from a corresponding control column that did not contain BRITC (results not shown).

Example 2

Cross-linking the Rhamnose Binding Protein and its Ligand

Materials/Methods (a) Labelling of Rhamnose Probes

Fluorescein Rhamnose-ITC (FRITC) was formed by reacting Rhamnose-ITC with fluorescein amine (Sigma F1148, RMM 347.3) at a molar ratio of 1:10 in 10 mM sodium bicarbonate pH 9.1.

(b) Cell Lysis

As per example 1.

(c) Multiple Surfactant Solution (MSS)

As per example 1.

(d) One-Dimensional Polyacrylamide Gel Electrophoresis (1D-PAGE)

As per example 1.

(e) Protein Visualisation In-Gel

As per example 1.

(f) Cell Probing

A2058 cells were coated at low density in a microscope compatible chamber. The cells were washed with $HBS^{2+}$ then incubated with FRITC (top concentration of DMSO= 2.5%) for 5–15 min at 37° C. The FRITC was removed, the cells washed twice with $HBS^{2+}$ and examined under a visible light microscope. The incubation was repeated with 0–100 μM fluorescein-amine, and for 25 and 6 μM FRITC using a $10^3$× excess of unlabelled rhamnose.

(g) Cell Surface Receptor Cross-Linking

A2058 cells prepared in 40 ml culture flasks were incubated with FRITC (5 or 10 μM) as described above and washed once with $HBS^{2+}$. Carbonyl di-imidazole (Aldrich 115533) was dissolved at 1M in DMSO immediately prior to use. This stock solution was then diluted in $HBS^{2+}$ or DMSO to 100 μM-10 mM and added to the cells at room temperature. After 15 min the cross-linker was removed and the flasks stored on ice. Cells were then removed from the flasks by scraping and taken up into MSS lysis buffer. Protein fractions were subjected to SDS-PAGE and the gels visualised as set out above.

(h) Two Dimensional Electrophoresis

Cross linked cells prepared according to method 7 above, using 5 μM FRITC, were lysed into 350 μl of MSS by cell scraping. This material was prepared for iso-electric focusing by loading onto an 18 cm Immobiline DryStrip, pH 3–10 [Amersham], the strip equilibrated and electrophoresed for approx. 150 kVhr (Voltage gradient: 200V, 12 hr; 250V, 1.5 hr; 500V, 2 hr; 1000V, 2.5 hr; 8000V, 19 hr).

The strip was then run in the second dimension using 1-D PAGE according to method 4 above, except a 10% polyacrylamide gel was used. The gel was analysed using a fluoroimager and silver stained.

Results

The electrophoretic profile of the protein components from the cross linking experiments are set out in FIGS. 2A and 2B. FIG. 2A depicts the proteins cross-linked to fluorescein that were visualised by fluorescence scanning and FIG. 2B depicts the total protein stained with Coomassie brilliant blue.

Figure 3:
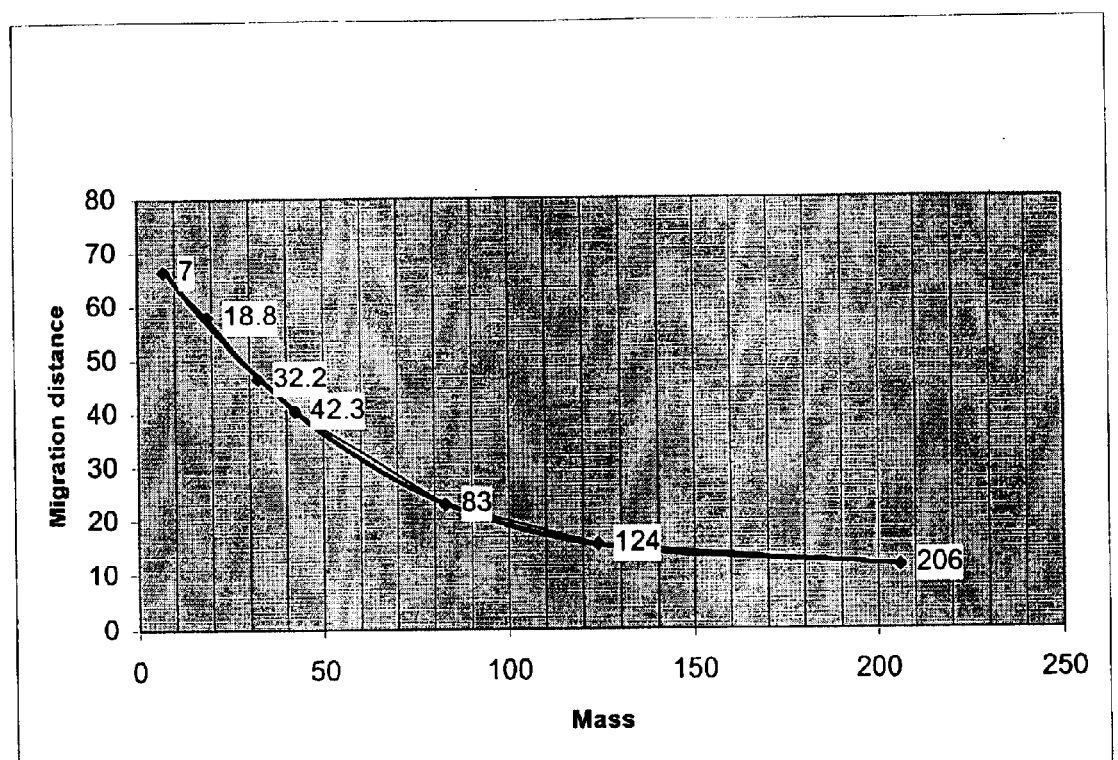
FIG. 3: is a graph used to calculate the molecular mass of the proteins in FIG. 2A.

The total protein stain indicates that there are approximately equal amounts of protein loaded in each lane. Following FRITC incubation two fluorescently labelled proteins are detectable that are not present in the CDI only lanes. Calibration of the gel using the molecular mass markers (FIG. 3) gives masses of 22 kD and 68 kD for these proteins. However, these masses include one or more FRITC molecules and consequently the mass of the receptor is approximately 67 kD.

The results from the two dimensional electrophoresis suggest the fluorescein tagged protein is running with a pI of approximately 6–7, and the molecular mass is consistent with prior results.

Example 3

Staining of Cells with a Fluorescein Tagged Rhamnose Probe (FRITC)

Materials/Methods

A fluorescein tagged rhamnose probe (FRITC) was prepared as previously described and used to stain A2058 cells.

FRITC at concentrations from 3–25 μM was incubated with A2058 cells for 15 minutes at 37° C.

Results

Figure 4:
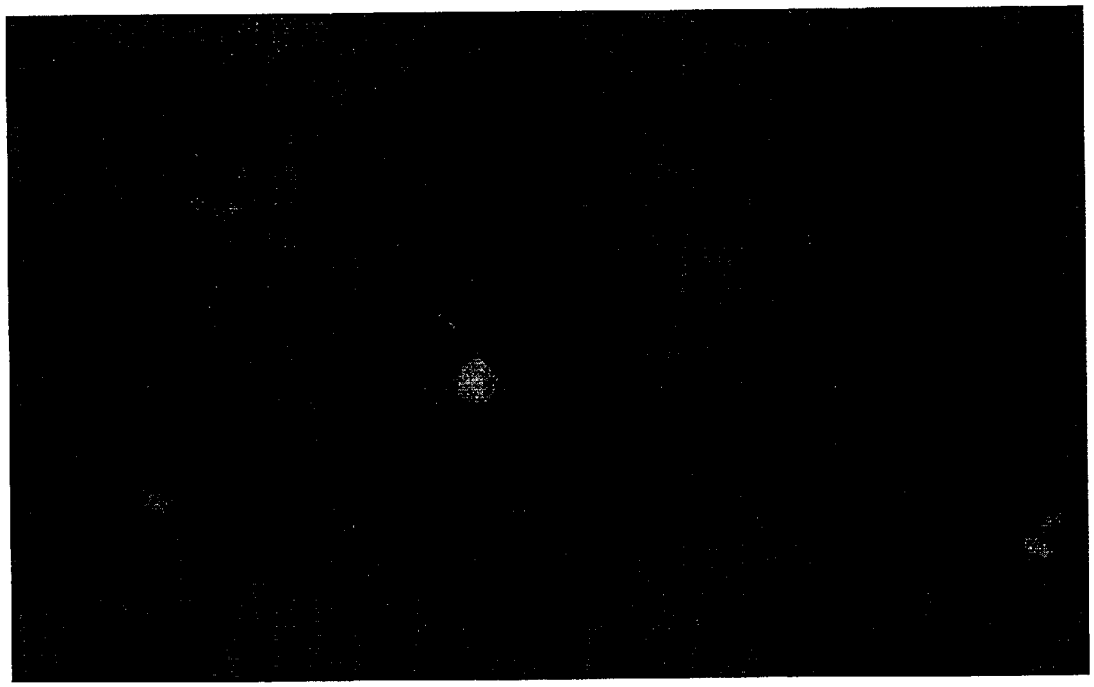
FIG. 4: is an image of A2058 cells following incubation with 12 μM fluorescein rhamnose-ITC at 37° C. for 15 min in HEPES buffered saline containing 2 mM $Ca^{2+}$ and $Mg^{2+}$.

The cells following incubation were found to fluoresce confirming the presence of a rhamnose binding protein on the cells. An image of the cells is depicted in FIG. 4 and closer inspection of the stained cells indicates an increased concentration of staining in the cell nucleus, suggesting the rhamnose probe is also taken inside the nuclear membrane. It was found that the staining could be inhibited by co-incubation of the FRITC and cells with free rhamnose at 10 mM concentration.

Example 4

Effect of Cell Density on Measured $LD_{50}$ Values

Materials/Methods

Given that the evaluation of the cytotoxicities for different cell lines needed to be conducted using different sized cell populations, it was considered prudent to determine the effect, if any, of cell number on the measured value of $LD_{50}$. Five cell lines, HT-29, LS174-T, 5637, A431 and MCF-7 were evaluated at four different seeding cell densities. Hs578T and CCD 18Lu were evaluated at three seeding densities and Hs578Bst, both early and late passage cells, were evaluated at two seeding densities.

In order that the full range of cell densities be evaluated with at least one cell line, a 3-day version of the cytotoxicity was developed. The cell lines involved were recalibtrated for the 3-day format. Multiwell plates were seeded on day 1. Cells were treated with BEC® on day 2 and MTT was added twenty four hours later.

Results

Figure 5:
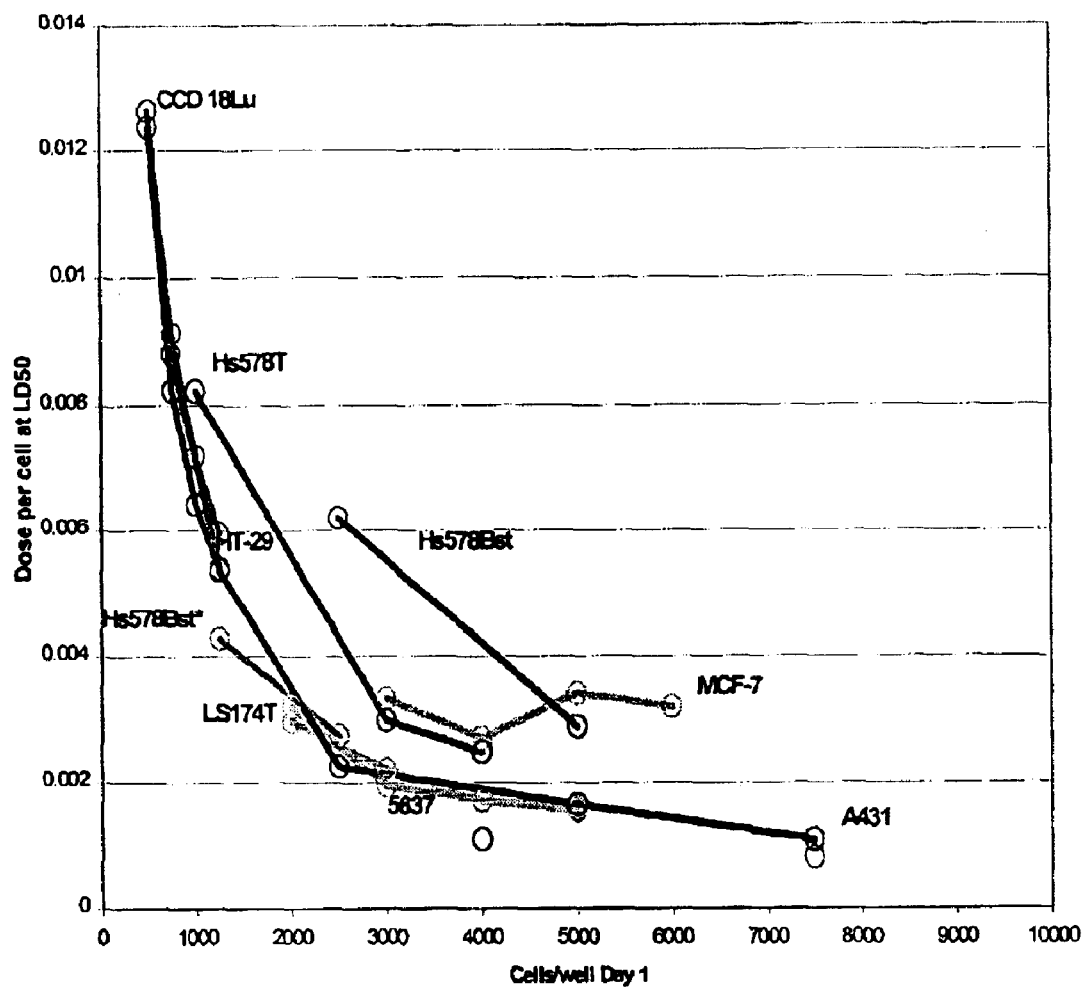
FIG. 5: is a plot of the relationship between dose per cell at $LD_{50}$ and the Day 1 cell density for each cell line.

Plotting the relationship between dose per cell at $LD_{50}$ and the Day 1 cell density for each cell line, FIG. 5, reveals that the behaviours of the epidermoid adenocarcinoma A431, the colorectal adenocarcinoma HT-29 and the normal infant lung fibroblast line, CCD 18Lu, are identical. Similarly, the plots for the colon adenocarcinoma LS174-T and the bladder carcinoma 5637 are almost coincident.

Figure 6:
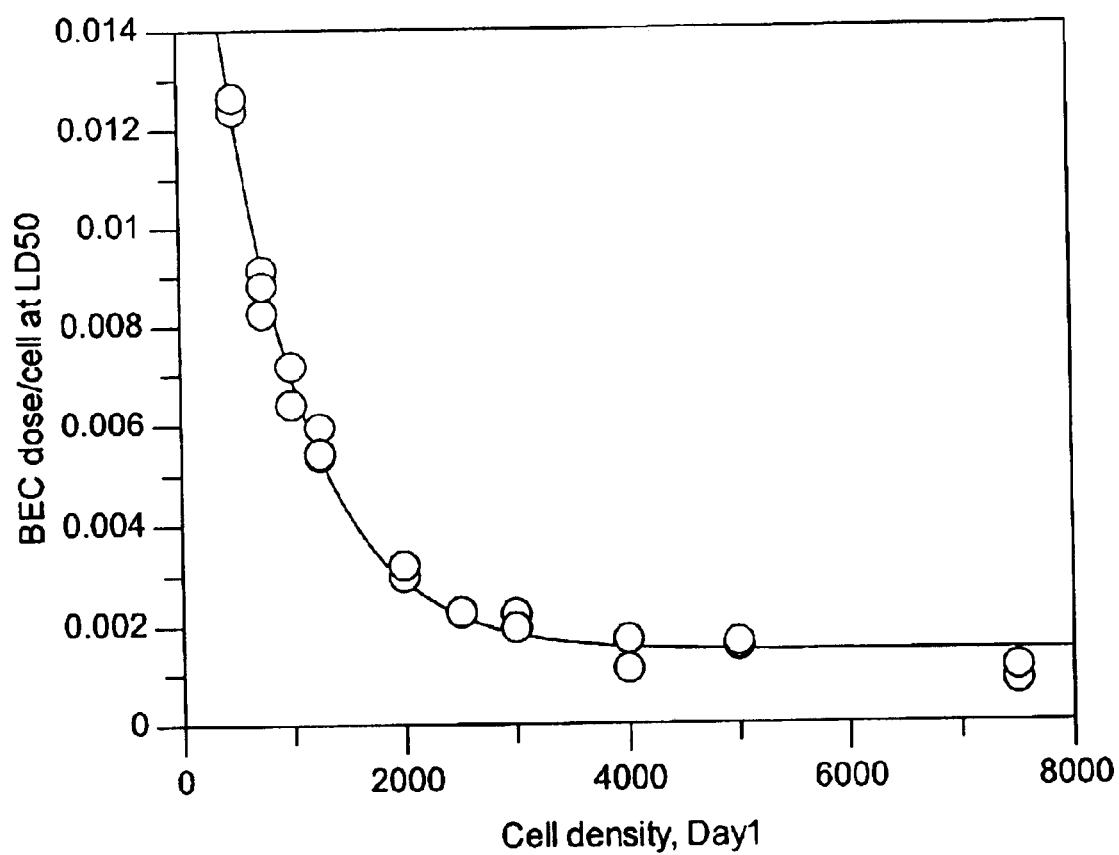
FIG. 6: depicts the data in FIG. 5 condensed and fitted to a single exponential function.

In fact, data from CCD 18Lu, A431, HT-29, LS174T and 5637 can be combined and fitted to a single exponential function, $$\text{Dose per seeded cell at } LD_{50} = \text{Intercept} \times e^{-k \times Seeding\ density} + \text{Limit}$$

as shown in FIG. 6.

This implies that, for these five cell lines the processes of BEC® uptake, including receptor affinity, hydrolytic processing to produce the lysogenic ligand complex, as well as the pathway to cell death, are quantitatively identical.

Figure 7:
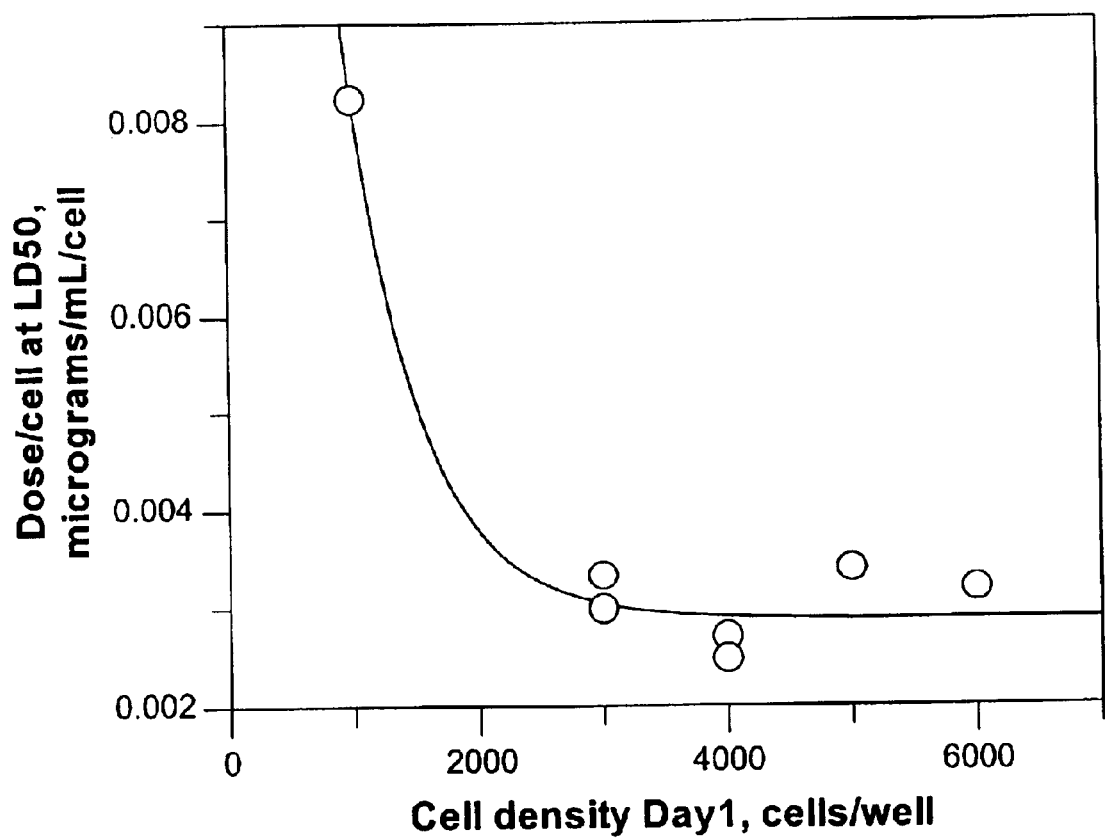
FIG. 7: is a plot of the relationship between dose per cell at $LD_{50}$ and the Day 1 cell density for two particular breast cancer lines.

Similarly, data from the two breast cancer lines, Hs578T, an infiltrating ductal carcinoma and MCF-7, a metastasis from a breast adenocarcinoma, appear to behave similarly to each other but differently from the other lines. These combined data sets can also be fitted to an exponential function, see FIG. 7.

Comparing the two fitted functions, two distinct regions are discernable (FIG. 8). The functions are virtually coincident at cell densities of 1,500 cells per well and below, conditions under which receptor affinity can be expected to be the major determinant of cytotoxicity (region 1 of FIG. 8). This suggests that only a single type of receptor is involved in virtually all cell lines included in this study. We estimate that the dissociation constant for this receptor is likely to be of the order of $1.5 \times 10^{-6}$ M.

However, the functions diverge at cell densities greater than 1,500 cells per well (region 2 of FIG. 8). The difference between the limit values, representing the minimum dose per cell to kill 50% of the susceptible population, is obvious. For LS174-T and 5637 the fitted value of this minimum dose is 300 pg BEC®/cell (71 pg solamargine/cell) while for the breast cancer lines this minimum dose is some three-fold higher at 580 pg BEC®/cell (137 pg solamargine/cell). Such a difference could arise from either a significantly lower number of receptors per cell or slower intracellular processing to produce the isolated ligand complex.

Note from FIG. 5 that the behaviour of early passage normal breast fibroblasts differs from late passage cells of the same line. Within the limitations of the restricted data sets these non-tumour cells appear to become more vulnerable to BEC® as they approach senescence.

Example 5

Single Point Data for Other Cell Lines

Materials/methods

A range of other cell lines were assessed in a similar manner to the assessments carried out in Example 4.

Results

Figure 10:
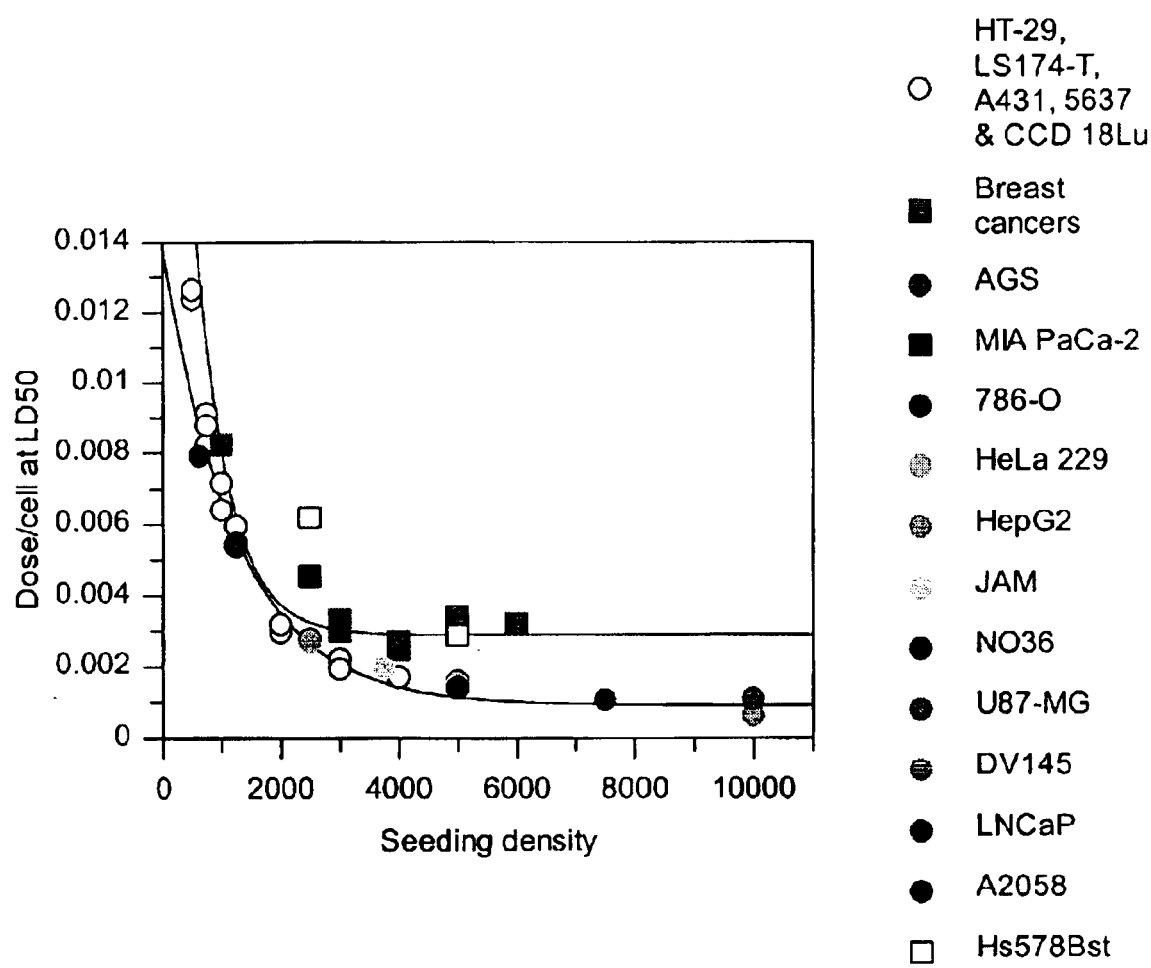
FIG. 10: is a graphical representation of the data presented in the table in FIG. 9.

FIG. 10 shows that the single data points for the other cell lines evaluated are plotted, with the exception of MIA PaCa-2, the breast cancer lines and the early passage normal breast fibroblasts, all fall on the same exponential curve of FIG. 6.

Example 6

Co-Administration of BEC® and Rhamnose

Materials/Methods

A2058 cells at two different cell densities were treated with BEC®+/−rhamnose and cell survival was monitored after 4 days. The treatments comprised: (i) BEC® only for 4 days (ii) BEC® only for 5 minutes (iii) BEC® and 5 mM rhamnose for 4 days and (iv) BEC® and 5 mM rhamnose for 5 minutes.

Results

Figure 11:
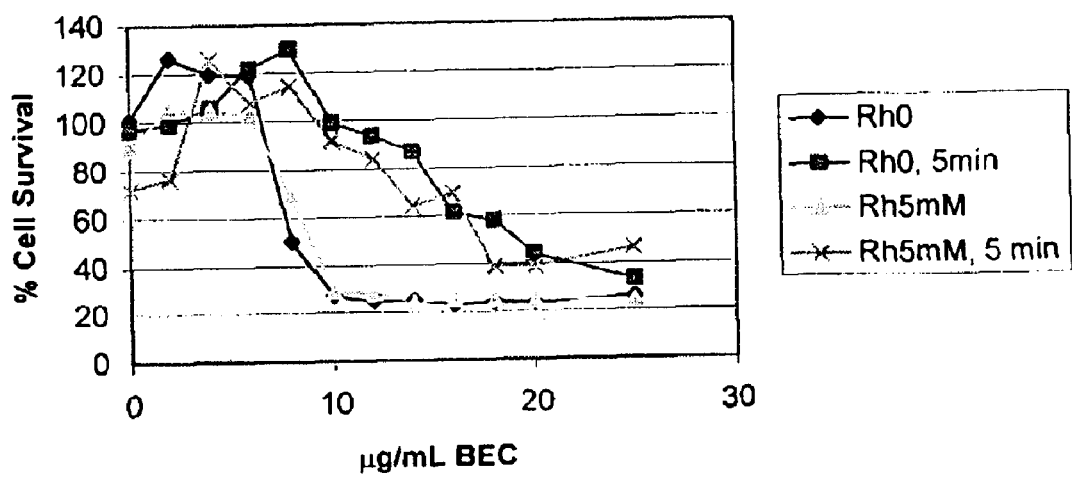
FIG. 11: illustrates the protective effects of rhamnose when co-administered with BEC® via a graph of % cell (A2058, 600 cells) survival v's concentration of BEC®.
Figure 12:
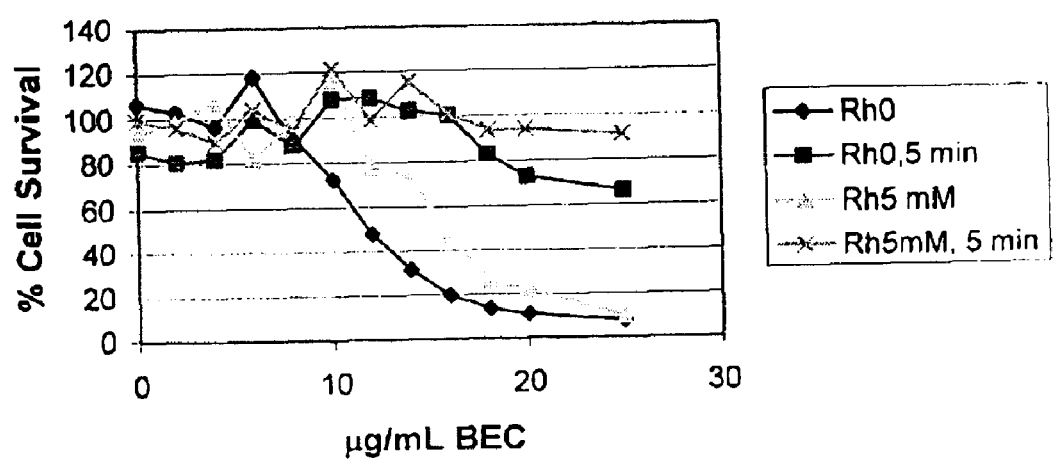
FIG. 12: illustrates the protective effects of rhamnose when co-administered with BEC® via a graph of % cell (A2058, 5000 cells) survival v's concentration of BEC®.

FIGS. 11 and 12 indicate that rhamnose competition with BEC® uptake is more readily observed at the higher cell density (5000 cells). Under these conditions, where the amount of BEC® available to each cell is a major factor determining $LD_{50}$, the presence of rhamnose at the relatively high concentration of 5 mM affects the amount of BEC® taken up by the cells in both 5 minutes and 4 days from solutions in specific concentration ranges. Data in FIG. 12 suggests that the rhamnose protective effect is more significant in the pulsed treatment experiment.

Example 7

Isolation of RBP

Materials/Methods
1. Preparation of FRITC
   The following reaction mixture was used:

| | |
|---|---|
| Rhamnose Isothiocyanate [Sigma R6881] | 5 mg/ml in 500 µl DMSO |
| Fluorescein [Sigma F 1148] | 50 mg in 500 µl |
| 100 mM sodium hydrogen carbonate | 120 µl |
| MilliQ water | 80 µl |

Incubate overnight at room temperature and store at −20° C. Purify FRITC by RP-HPLC:

Column: C18 reverse phase

Solvent A: water+0.06% tri-fluoro acetic acid (TFA)

Solvent B: 80% acetonitrile (ACN)/water+0.06% TFA

Analytical gradient 98–50% (A) over 15 min. Flow 1 ml/min. Wavelength 255 nm or 220 nm.

Preparative gradient 98% (A) for 2.5 min., 98–50% (A) over 20 min. Flow 2 ml/min. Wavelength 255 nm or 220 nm.

2. Cell Surface Receptor Cross-linking

A2058 cells were grown to 80–90% confluency in 25 ml culture flasks and then washed with 2×HEPES buffered saline containing 140 mM NaCl, 2 mM $MgCl_2$, and 2 mM $CaCl_2$, pH 7.4 ($HBS^{2+}$). FRITC was dissolved in a minimal volume of DMSO (5–10 µl) and added to 1 ml $HBS^{2+}$ to give a concentration of 2–10 µM FRITC. The FRITC solution was added to the cells and the flask incubated for 15 min at 37° C. The FRITC was removed, the cells washed once with $HBS^{2+}$, and freshly prepared carbonyl di-imidazole (100 µM in 1 ml DMSO) was added immediately at room temperature. After a minimum of 15 min the cross-linker was removed and the flasks stored on ice.

3. Protein Extraction Following Receptor Cross-linking

All the DMSO is aspirated from the cells and 300–400 µl of MSS (section 10) is added to the flask. The MSS is spread over the entire surface area of the flask and the cells then scraped using a cell scraper/harvester. The cells in MSS are allowed to incubate for 15 min at room temperature to remove as much of the protein as possible.

Cell extracts are removed from the flask and added to a fresh tube. The protein is precipitated by adding 1 ml of methanol (or acetone) and storing the sample over night at −80° C. To remove viscous material (e.g. DNA, lipid etc.) the tube was centrifuged for 30 min at 13000 rpm and 4° C. The methanol was removed and the sample resuspended in 300 µl of MSS. To this 1.2 ml of hexane was added and the sample again centrifuged for 30 min at 13000 rpm and 4° C. The top layer was discarded and any white particulate matter on the surface of the aqueous layer was also removed. Samples were then analysed by SDS-PAGE.

4. Immunoprecipitation of FRITC Cross-linked Proteins

100 µl of protein extract (section 1 above) was diluted to 10 ml with 50 mM Tris-Cl pH 7 and 0.05% Tween 20. In order to pre-clear non-specific binding material 50 µl of protein A sepharose [Amersham] was added and incubated overnight at 4° C. on a rotating wheel. After incubation, the sample was centrifuged at 2000 rpm for 5 min to pellet the sepharose. The supernatant was added to 10 µl of anti-FITC antibody [Sigma], 50 µl of protein A sepharose and incubated overnight at 4° C. on a rotating wheel. After incubation the sepharose was washed 2×1 ml with 10 mM Tris pH 7 and the whole sample (matrix included) was run on 4–20% SDS-PAGE. The gel was then assessed for FRITC labelled proteins by fluorescent detection.

5. 1D PAGE was Carried Out as in Example 1.

6. Protein Visualisation In-Gel

To detect fluorescently labelled proteins gels were scanned using a Fluoro-imager (Pharmacia): fluorescein excitation wavelength 494 nm, emission wavelength 520 nm.

Visual staining was accomplished either with Coomassie G250 in water/methanol/acetic acid or silver staining (PI in-house mass spectrometry compatible protocol; under optimised conditions this is approximately 10-fold less sensitive than previously used methods).

Results

1. Preparation of FRITC (Fluorescein Rhamnose Isothiocyanate)

Large quantities of fluorescein labelled rhamnose probe (FRITC) were purified by HPLC and their viability confirmed by mass spectrometry. The probe appears stable indefinitely if stored dry at −20° C.

2. Cell Surface Receptor Cross-linking

Cross linking of FRITC to the surface of A2058 cells was performed successfully in 25 ml culture flasks. Large scale FRITC cross-linking (75 ml flasks) using identical concentrations of reagent was unsuccessful. This suggests the reaction is readily influenced by micro-changes in the cell environment. Our observations also indicated that an advantageous side effect of using carbonyl di-imidazole cross linker was that the cells became adhered to the flask surface during the procedure and hence were easier to wash.

Figure 13:
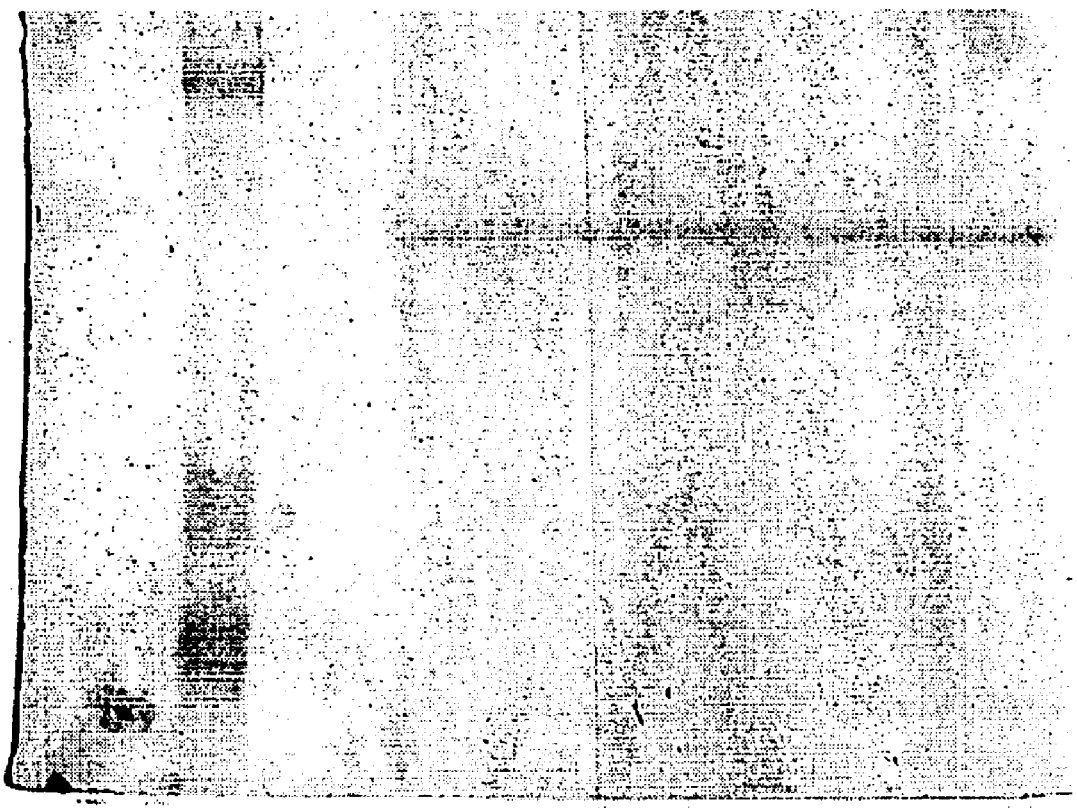
FIG. 13 illustrates a fluoro-image of A2058 proteins crosslinked to FRITC, solvent extracted and analysed on a 4–20% SDS polyacrylamide gel. From left, Lane 1: Standards 83, 42.3, 32.2, 18.8 kD; Lane 2 blank; Lanes 3–8: replicate flasks of cells+approx 5 $\mu$M FRITC+100 $\mu$M carbonyl di-imidazole.

A cross-linked FRITC protein complex was consistently visible on SDS-PAGE gels by fluorescent imaging (FIG. 13).

3. Protein Extraction Following Receptor Cross-linking

Our procedures have focused on maximising the yield of the FRITC-receptor complex, and subsequently isolating the complex from unwanted contaminants. The extraction procedures have involved different protein precipitation methods and subsequent solubilisation steps. The A2058 Receptor-FRITC complex appears fully soluble in multiple surfactant solution (SPRL21111), and partially soluble in a range of non-ionic detergents (2% Tween 20, 2% Triton X-100, 2% CHAPS), however no single non-ionic detergent has been identified that fully solubilises the complex.

Further, the fluorescent complex appears to be associated with the cell debris/DNA that is precipitated during the initial methanol precipitation. To overcome this problem (of contamination and viscosity) we have developed a two-stage clean-up using methanol, followed by hexane.

4. Immunoprecipitation of FRITC Cross-linked Proteins

Figure 14:
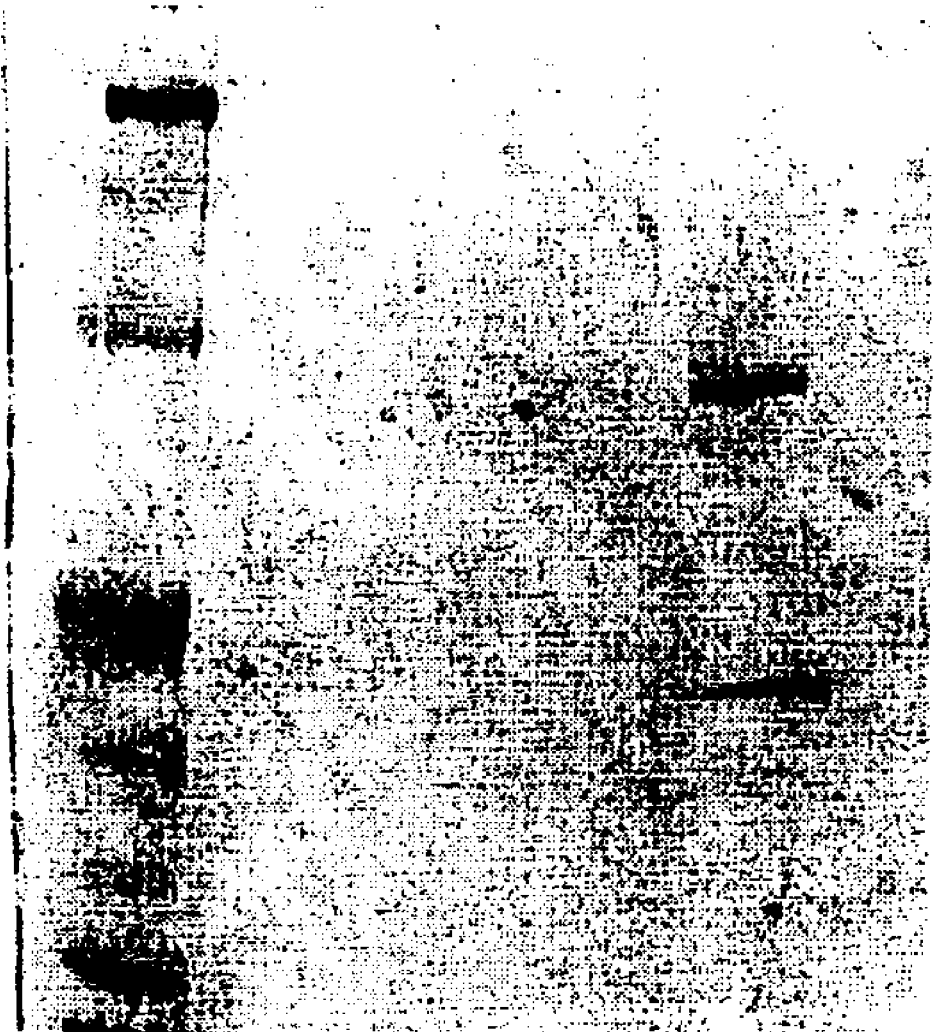
FIG. 14 illustrates immunoprecipitation of FRITC-protein cross-linked complex analysed on a 4–20% SDS polyacrylamide gel.

The protein-FRITC complex was diluted into a low detergent, low salt buffer and incubated with an antibody directed against fluorescein. Any complexes formed were absorbed onto protein A, precipitated and analysed by SDS-PAGE. The experiments produced a feint protein band at approx 70 kD that was detectable by Coomassie blue staining FIG. 14).

Further modifications and adaptations not specifically disclosed herein that are apparent to those skilled in the art upon reading this specification are encompassed within the scope of this invention.

REFERENCES

1. Ashwell, G and Harford, J. (1982) "Carbohydrate specific receptors of the Liver". Ann Rev. Biochem, 51, 531–554.
2. Lehrman, M A. et al (1986) "The binding of fucose containing glycoproteins by hepatic lectins". J. Biol. Chem., 261 (16) 7412–7418.
3. Kolb-Bachofen, V. et al (1984) "Gal/NAC/Gal specific rat liver lectins their role in cellular recognition". Biol. Cell, 51, 219–226.
4. Cramer, F. and Gabius, H J. (1991) U.S. Pat. No. 5,225,542.

What is claimed is:

1. An isolated rhamnose binding protein (RBP) comprising a molecular weight of about 65 kDa to about 70 kDa as determined by SDS-PAGE, wherein the RBP is insoluble in aqueous solution and over expressed in cancer cells as compared to non-cancer cells.

2. An isolated RBP according to claim 1, comprising a molecular weight of about 66 kDa to about 69 kDa.

3. An isolated RBP according to claim 1, comprising a molecular weight of about 67 kDa.

4. An isolated RBP according to claim 1, further comprising one or more of the following characteristics:

a) a pI of greater than 10 or less than 3;
　b) a dissociation constant of about $1.5 \times 10^{-6}$ when bound to rhamnose moiety of solamargine;
　c) binds to a rhamnose affinity column in the from of a streptavidin sepharose conjugated column or free resin with a theoretical capacity for biotin rhamnose ITC (BRITC) of 60 µg/ml, wherein the BRITC is coupled to the column by passing a phosphate buffered solution comprising an excess of BRITC dissolved therein over the column at a flow rate of about 0.2 ml/min for 30 minutes;
　d) elutes from the rhamnose affinity column in c) with a 100 mM rhamnose solution; or
　e) soluble in a denaturing buffer comprising at least about 2% surfactant.

5. An isolated RBP according to claim 1, further comprising the following characteristics:

a) a pI of greater than 10 or less than 3;
　b) a dissociation constant of approximately $1.5 \times 10^{-6}$ when bound to rhamnose moiety of solamargine;
　c) binds to a rhamnose affinity column in the column of a streptavidin sepharose conjugated column or free resin with a theoretical capacity for biotin rhamnose ITC (BRITC) of 60 µg/ml, wherein the BRITC is coupled to the column by passing a phosphate buffered solution comprising an excess of BRITC dissolved therein over the column at a flow rate of about 0.2 ml/min for 30 minutes;
　d) elutes from the rhamnose affinity column in c) with a 100 mM rhamnose solution; and
　e) soluble in a denaturing buffer comprising at least about 2% surfactant.

6. An isolated RBP according to claim 1, wherein the cancer cells are human.

7. An isolated RBP according to claim 1, wherein the RBP is isolated from cancer cells.

8. An isolated RBP according to claim 7, wherein the cancer cells are AGS cells, MIA PaCa-2 cells, 786-O cells, HeLa 229 cells, HepG2 cells, JAM cells, NO36 cells, U87-MG cells, DV145 cells, LNCaP cells, or A2058 cells.

9. An isolated RBP according to claim 7, wherein the cancer cells are HT-29 cells, LS174-T cells, 5637 cells, A431 cells, Hs578T cells, CCD 18 Lu cells, or MCF-7 cells.

* * * * *